United States Patent [19]

Huzinec

[11] Patent Number: 4,741,905

[45] Date of Patent: May 3, 1988

[54] CHEWING GUM CANDY

[75] Inventor: Robert Huzinec, Kenvil, N.J.

[73] Assignee: Warner-Lambert Company, Morris Plains, N.J.

[21] Appl. No.: 876,945

[22] Filed: Jun. 19, 1986

[51] Int. Cl.⁴ .............................................. A23G 3/30
[52] U.S. Cl. ...................................... 426/3; 426/658; 426/804; 426/660
[58] Field of Search .................. 426/3, 4, 5, 660, 804, 426/658

[56] References Cited

U.S. PATENT DOCUMENTS

| | | | |
|---|---|---|---|
| 193,045 | 7/1877 | Sibley | 426/3 |
| 2,460,698 | 2/1949 | Lindhe | 426/5 |
| 3,857,965 | 12/1974 | Ream | 426/3 |
| 3,862,338 | 1/1975 | Sapsowitz | 426/3 |
| 4,614,654 | 9/1986 | Ream et al. | 426/5 |

FOREIGN PATENT DOCUMENTS 0026355  3/1978  Japan ......................................... 426/3

*Primary Examiner*—Jeanette Hunter
*Attorney, Agent, or Firm*—Charles A. Gaglia, Jr.; Gary M. Nath

[57] ABSTRACT

A chewing gum candy confection product prepared by mixing a melted chewing gum base with a cooked hard candy sorbitol syrup at a temperature which renders the gum base and the cooked candy syrup miscible under mild blending conditions to form a substantially single phase continuous plastic chewing gum candy mass. The mass is mildly blended under controlled cooling so that substantially no air is introduced into the mixture. Additives such as flavoring, coloring and bio-effecting agents are optionally incorporated under continued mild blending conditions. Finally, the product is cooled to a hard candy matrix containing chewing gum therein, such matrix suitable for scoring and cutting and for grinding into a particulate and/or a powder.

12 Claims, No Drawings

CHEWING GUM CANDY

BACKGROUND OF THE INVENTION

The present invention relates to the art of chewing gum confections, and, in particular, to a gum-containing candy product.

It has been known in the art of confections to provide chewing gum products with high sweetness levels which can include candy components. Such products are known for, among other things, their appeal as novelty confections. These confections can be sugar-containing or sugarless, depending on the desired product.

For example, U.S. Pat. No. 2,460,695 discloses a candy chewing-gum having a hard, candy-like appearance and a longer shelf life than conventional chewing-gum products. However, the process for making requires mixing gum base with sugar in its hot liquid state, thereby resulting in a mixture which is too viscous to be cast; it must be extruded or pulled to produce the final gum product. Furthermore, the sugar chars upon heating in its liquid state.

Japanese publication 5 3026-355 discloses a preparation of a chewing gum which includes mixing 20–40% by weight of gum base and 60–80% by weight of material for hard candy in melted state at elevated temperature, following by foaming the mixture by kneading or agitating at 55°–100° C., and solidifying by cooling the mixture after expansion at reduced pressure and elevated temperature. The candy material includes 40–80% sugar by weight, 20–60% by weight of starch syrup (or sugar alcohol consisting of 7–18 glucose units) and 1.5–4% by weight of water, and the gum base includes a resin component, such as vinyl acetate and natural chicle, and glycerin ester of polyisobutylene-rosin and polybutene. The candy material and base should be miscible and have proper viscoelasticity at >115° C. The process requires foaming by bubbling air into the mixture under agitation. The foamed product is then expanded to a volume of 120–400%, having an apparent density of 0.31–1.13. The process results in a porous chewing gum which hardens upon aging, but does not in any way suggest a hard candy matrix product which can include chewing gum in the matrix for scoring or grinding into a particulate.

U.S. Pat. No. 4,271,199 to Cherukuri, et al. discloses a chewing gum with a soft, smooth, consistency, and an amorphous bite through which includes a premixed recrystallized combination of liquid and solid sweeteners. Preferably, the Cherukuri, et al. product includes high fructose syrup alone or together with liquid glucose, corn syrup, sorbitol syrup and/or invert sugar in combination with sucrose or sorbitol and water, and flavors, softeners, and other conventional chewing gum ingredients. The formulation has a short nougat-like or fondant-like structure and is particularly suitable as a non-stick bubble gum which does not stick to its wrapper. It is essential to the Cherukuri, et al. U.S. Pat. No. 4,271,199 composition that the liquid and solid sweeteners comprise a preformed combination of particulate solid sweetener particles which are coated with a syrup sweetener, and that the mixture be heated, dried to a homogeneous mass, and then cooled to recrystallize the mass into an amorphous solid. The confection resulting from the composition of Cherukuri, et al. U.S. Pat. No. 4,271,199 is a chewing gum having a nougat-like texture.

U.S. Pat. No. 3,857,965 to Ream describes a method for making a chewing-gum composition which includes melting crystalline sorbitol or concentrating a sorbitol solution by heating, mixing chewing-gum base and a crystallization retardant with the sorbitol, homogenously blending and then forming the mixture, either by casting into a mold or by product-forming after cooling to a viscous state. Inasmuch as sorbitol composition will re-crystallize and become crumbly upon standing it is necessary to add crystallization retardant.

None of the above-products, however, provide a quick set hard candy matrix which includes a chewing gum and which can be ground to a particulate for use with other confection products.

SUMMARY OF THE INVENTION

The present invention is a chewing gum candy confection product prepared by mixing a melted chewing gum base with a cooked hard candy syrup at a temperature which renders the gum base and the syrup miscible under mild blending conditions to form a substantially single phase continuous plastic chewing gum candy mass. The mass is then mildly blended under controlled cooling so that substantially no air is introduced into the mixture, after which flavoring, flavor enhancers and coloring as well as other additives can optionally be included under continued mild blending conditions. Finally, the mass is cooled to a hard candy matrix having chewing gum pieces contained therein. The matrix is suitable for scoring and cutting, and can be ground into a particulate for use in the other confection products. The candy product has a specific density of from about 1.20 to about 1.50, and preferably is about 1.32.

Preferably the base is included in an amount of from about 5 to about 55% by weight, and most preferably from about 15 to about 40% by weight, while the cooked hard candy syrup is included in an amount of from about 45% to 95% by weight, and preferably from about 60% to about 83% by weight.

The hard boiled candy syrups can be prepared from a mixture of sugar and other carbohydrates. Such materials may normally contain up to 100% corn syrup, up to 70% sugar and from 0.1% to 5.0% water. The syrup component generally is prepared from corn syrups high in dextrose or maltose but may include other materials. Further ingredients such as flavorings, sweeteners, acidulents, colorants and so forth may also be added.

Boiled candy syrups can also be prepared from non-fermentable sugars such as sorbitol, mannitol, xylitol and maltitol and syrups thereof such as hydrogenated starch hydrolyzates and sorbitol solutions. A typical hydrogenated starch hydrolyzate is Lycasin (a trademark of Roquette Corp.). The candy syrups may contain up to about 95% sorbitol, a mixture of sorbitol and mannitol, or other sugar alcohols at a ratio of about 9.5 to 0.5 up to about 7.5 to 2.5 and hydrogenated corn syrup up to about 95% of the syrup component.

In one embodiment the hard candy syrup includes 40% to about 75% corn syrup by weight, 25% to about 48% by weight sugar and up to about 8% by weight of water, and is cooked to a temperature of from about 127° to 155° C. for about two to six minutes before adding the melted chewing gum base. The blending can be conducted at a temperature of from about 127° to about 138° C. for about two to six minutes.

In another embodiment, the hard candy syrup includes substantially sorbitol syrup cooked to a temperature of from about 171° to about 185° C. before adding the melted chewing gum base.

The gum base can include an elastomer selected from the group consisting of natural and synthetic elastomers. For example, those elastomers which are suitable in gum bases, include, without limitation, substances of vegetable origin such as chicle, jelutong, gutta percha, guayle and crown gum. Synthetic elastomers such as butadiene-styrene copolymers, isobutylene-isoprene copolymers, polyethylene, polyisobutylene and mixtures thereof, are particularly useful.

The gum base composition may contain elastomer solvents to aid in softening the polymer component. Such elastomer solvents can include methyl, glycerol or pentaerythritol esters of rosins or modified rosins, such as hydrogenated, dimerized or polymerized rosins or mixtures thereof. Examples of elastomer solvents suitable for use herein include pentaerythritol ester of partially hydrogenated wood rosin, pentaerythritol ester of wood rosin, glycerol ester of partially dimerized rosin, glycerol ester of polymerized rosin, glycerol ester of tall oil rosin, glycerol ester of wood rosin, and partially hydrogenated wood rosin, and partially hydrogenated methyl ester of rosin and mixtures thereof. The solvent may be employed in an amount ranging from about 10% to about 75% and preferably about 45% to about 70% by weight of the gum base. In order to include the gum base into the cooked hard candy syrup, it is preferably heated to a temperature of from 82° to about 94° C.

A variety of traditional ingredients used as plasticizers or softeners such as lanolin, stearic acid, sodium sterate, potassium stearate, glyceryl triacetate, triacetin, glycerine and the like, can also be incorporated into the gum base to obtain a variety of desirable textures and consistency properties. These additional materials are generally employed in amounts of up to about 30% by weight and preferably in amounts of from about 3% to about 7% by weight of the final gum base composition.

The chewing gum candy composition of this invention may additionally include the conventional additives of coloring agents such as titanium dioxide; emulsifiers such as lecithin and glyceryl monostearate; and fillers such as dicalcium phosphate, aluminum hydroxide alumina, aluminum silicates, talc, calcium carbonate, and combinations thereof. The total amount of fillers present is generaly between 4% and 30% by weight. Flavoring agents well known to the chewing gum and candy art may be added to the chewing gum candy compositions of the instant invention. These flavoring agents may be chosen from synthetic flavor oils and/or oils derived from plants, leaves, flowers, fruits and so forth, and combinations thereof. Representative flavor oils include: spearmint oil, cinnamon oil, oil of wintergreen (methysalicylate) and peppermint oils. Also useful are atrificial, natural or synthetic fruit flavors such as citrus oil including lemon, orange, grape, lime and grapefruit, and fruit essences including apple, strawberry, cherry, pineapple and so forth.

The amount of flavoring agent and/or flavor enhancers employed is normally a matter of preference subject to such factors as flavor type, base type and strength desired. In general, amounts of about 0.05% to about 3.0% by weight of the final candy chewing gum composition are useable with amounts of about 0.3% to about 1.5% being preferred and about 0.7% to about 1.2% being most preferred.

The chewing gum hard candy confection of the present invention can be used as a delivery system for an active ingredient such as a bio-effecting agent selected from the group consisting of mineral supplements, analgesics, antipyretics, antiarrhythmics, ion exchange resins, appetite suppressants, vitamins, anti-inflammatory substances, coronary dilators, cerebral dilators, peripheral vasodilators, anti-infectives, psychotropics, antimanics, stimulants, antihistamines, laxatives, decongestants, gastro-intestinal sedatives, antidiarrheal preparations, anti-anginal drugs, vasodilators, anti-hypertensive drugs, vasoconstrictors and migrane treatments, antibiotics, tranquilizers, antipsychotics, antitumor drugs, anti-coagulants and antithrombotic drugs, hypnotics, sedatives, anti-emetics, anti-nauseants, anticonvulsants, neuromuscular drugs, hyper and hypoglycaemic agents, thyroid and antithyroid preparations, diuretics, antispasmodics, uterine relaxants, nutritional additives, anti-obesity drugs, anabolic drugs, erythropoietic drugs, antiasthmatics, expectorants, cough suppressants, mucolytics, anti-uricemic drugs and mixtures thereof.

The product produced in the present invention is a hard candy product which is ideally suited for grinding into a particulate for use in other confection products, and has an initial hardness of from about 9.52 lbs. to about 12.84 lbs. when subjected to a penetrometer test by use of Instron test equipment. The hardness tests were performed using an Instron Corp. Model 1133 penetrometer machine, with a crosshead speed of 0.5 inches/minute. A 3/16 inch bit plunger and small annulus was used to determine the hardness of the sample. When used in a form of a particulate, it has been found that a suitable particulate size is from about 40 to about 200 mesh depending upon final usage, which can be used as a coating or otherwise incorporated into other confection products merely by incorporation during a mixing process. The product can be further ground to a powder when desired.

As a result of the present invention, a chewing gum candy confection product can be produced which has a quick setup time and which is essentially a hard candy matrix enclosing the chewing gum base as well as other desired additives. The products can be used, for example, to extend the duration of flavor or, alternatively, as a powdered candy gum to use with other confection products to enhance the texture, flavor and other organoleptic qualities of the product. Furthermore, the particulate or powder can also be used with active ingredients included before setup time or can be mixed with active ingredients to provide a sustained delivery system for such actives.

Other uses of the present invention include forming the particulate into a tableted chewing gum confection product. Also it has been considered useful as a center-filling to provide a candy chewing gum product within a gum or within another hard candy product.

For a better understanding of the present invention, together with other and further objects, reference is made to the following description, and the scope of the invention will be pointed out in the appended claims.

DETAILED DESCRIPTION OF THE INVENTION

The present invention is a chewing gum hard candy confection, which softens in the mouth to a chewable mass upon mastication, and can be prepared by mixing a melted gum base with a cooked hard candy syrup with or without the presence of a vacuum. The range of the components of the present invention are shown in the following table.

TABLE I
GENERAL FORMULA FOR CHEWING GUM HARD CANDY CONFECTION

| Ingredient | % By Weight |
| --- | --- |
| Cooked Hard Candy Syrup | 45 to 95 |
| Chewing Gum Base | 5 to 55 |

The base material is heated to a temperature of from about 82° C. to about 94° C. before blending with the cooked hard candy syrup, which is cooked to a temperature of from about 127° to about 185° C. for a time of about from two to six minutes depending on whether the product is sugar or sugarless.

Preferably, the two components are included in the following preferred ranges in order to obtain the best chewing gum hard candy product.

TABLE II
PREFERRED FORMULA FOR CHEWING GUM HARD CANDY PRODUCT

| Ingredient | % By Weight |
| --- | --- |
| Cooked Hard Candy Syrup | 60 to 83 |
| Chewing Gum Base | 15 to 40 |

The gum base and hard candy syrup should be mixed under mild blending conditions under controlled cooling until the resulting mixture reaches the temperature of from about 60° to 70° C., at which point flavoring, coloring and other additives can be incorporated without fear of losing the additives from flash off.

The resulting plastic mass can then be further cooled to 50° to 60° C. at which point the product can be rolled and scored into pieces for packaging. Alternatively, the stiff plastic mass can be subjected to grinding, e.g., as in a blender, until it is ground to either a particulate or even a powder consistency for use in other confection products. This unique grindable chewing gum hard candy composition can be used as a delivery system by incorporating bio-effecting additives as previously set forth in the cooked mass and/or adding active ingredients to the particulate or powder form attained by grinding, which can be tabletted if desired.

The product of the present invention can also be made as a sugarless hard candy product by using sorbitol syrup as the hard candy syrup.

SPECIFIC EXAMPLES OF THE INVENTION

EXAMPLE 1

A chewing gum hard candy confection was produced by first preparing a hard candy syrup in accordance with the following formula.

TABLE III
HARD CANDY SYRUP

| Ingredient | % By Weight |
| --- | --- |
| Corn Syrup 42 D.E. | 56.40 |
| Sugar | 37.00 |
| Water | 6.60 |
| | 100.00 |

The above ingredients were mixed together and cooked to a temperature of 132° to 149° C. for a period of from about two to about six minutes.

To the above hard candy syrup was added a chewing gum base which included as the primary components, styrene butadiene rubber (SBR) elastomer, and polyvinyl acetate resin, as well as plasticizers for compatibilizing the resin and the elastomer components.

The following formula was used:

TABLE IV
CHEWING GUM HARD CANDY CONFECTION

| Ingredient | % By Weight |
| --- | --- |
| Hard Candy Syrup | 78.80 |
| Gum Base | 20.00 |
| Spearmint/Peppermint Flavor | 1.20 |
| | 100.00 |

The gum base was melted by heating to a temperature of from about 82° to about 94° C. and then mixed under mild mixing conditions with the hard candy syrup. The ingredients were blended together under controlled cooling conditions until a temperature of about 61° C. was reached at which point orange flavor was added in an amount of about 1.2% based on the entire composition.

The product prepared in accordance with the above ingredients was then rolled and scored, a portion of the mass being separated for subsequent grinding in a blender. Surprisingly, the blender was able to effect an even grinding to a particulate and then to a powder without agglomeration of particles sticking to the blades and/or the sides of the blender. This is quite unexpected in view of the adhesive nature of the ingredients.

The product both in the hard candy form and in the particulate form was a very sweet product which was broken down in the oral cavity to a chewable mass. The combination of the sweetness level as well as the texture of the product produced a highly desirable organoleptic quality which has been deemed quite useful both as a confection product, and as a additive to other confection products.

EXAMPLE 2

A second product was prepared using the same formula as set forth above with regard to the hard candy syrup, but the proportion of gum base to candy syrup was changed somewhat. The chewing gum hard candy confection was prepared in accordance with the following formula.

TABLE V
CHEWING GUM HARD CANDY CONFECTION PRODUCT

| Ingredient | % By Weight |
| --- | --- |
| Hard Candy Syrup | 68.80 |
| Gum Base | 30.00 |
| Spearmint/Peppermint Flavor | 1.20 |
| | 100.00 |

The above confection product was prepared basically as set forth in Example I except that the syrup was cooked to a temperature of only 132° C. before the gum base was added. The resulting product was then rolled to a slab and cut into chunks as well as a portion being subjected to grinding as in the first Example. Once again the resulting product was a very sweet chewing gum-containing hard candy product which upon introduction into the oral cavity was eventually broken down to a chewable mass which retained a high level of sweetness.

EXAMPLE 3

A sugarless chewing gum hard candy confection product was prepared by using sorbitol syrup in the place of the hard candy syrup set forth above. Basically, the sorbitol solution contained 70% solids and was cooked to 180° C. before the syrup was blended with the melted base. The formula for the sugarless sorbitol containing chewing gum hard candy confection product is as follows.

TABLE VI
SUGARLESS CHEWING GUM HARD CANDY CONFECTION PRODUCT

| Ingredient | % By Weight |
| --- | --- |
| Sorbitol Solution | 78.80 |
| Gum Base | 20.00 |
| Spearmint/Peppermint Flavor | 1.20 |
| | 100.00 |

After mild blending and cooling, the resultant mass was rolled, scored and part of it was also subjected to grinding in a blender. The product, as in the sugar-containing composition, was an excellent highly-pleasing hard candy product which had good sweetness level as well as sustained sweetness and good final organoleptic property as a chewable mass.

As previously indicated, penetrometer tests were conducted on specimens resulting from the above Examples using an Instron Corp. 1133 penetrometer with a 3/16 inch bit plunger and accommodating annulus. The initial hardness of the candy was determined to be from about 9.52 lbs. to about 12.84 lbs. with a crosshead speed of 0.5 inches/minute.

As an added feature, it has been found that the Examples prepared in accordance with the above procedures can also be worked while still warm, i.e., at a temperature of about 50° to 60° C., to obtain any result desired by the skilled artisan.

In addition to the use of sorbitol solution, it is believed that other sugarless compositions can be used which include, for example, hydrogenated starch hydrolyzates, mannitol, xylitol, maltitol, or any other sugar alcohol or, in fact, combination thereof with artificial sweeteners in order to produce the desired result. The artificial sweeteners can include, but are not limited to, solid natural or synthetic sweetener such as amino acid based sweeteners, dipeptide sweeteners, especially aspartame, glycyrrhizin, saccharin and its salts, acesulfame salts, cyclamates, steviosides, talin, dihydrochalcone compounds and mixtures thereof.

Finally, it is also contemplated to be able to use the present confection with active bio-effecting agents as set forth above, both incorporated within the hard candy confection before grinding and mixed therewith in order to obtain an initial and as well as a sustained release of the active while in the oral cavity.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A sugarless chewing gum candy confection product prepared by the process comprising:
   mixing a melted chewing gum base heated to a temperature of from about 82° C. to about 94° C. with a cooked hard candy syrup of sorbitol at a temperature which renders said gum base and said cooked candy syrup miscible under mild blending conditions to form a substantially single phase continuous plastic chewing gum candy mass,
   mildly blending the resulting mixture under controlled cooling to a temperature of from about 60° C. to about 70° C. so that substantially no air is introduced into said mixture, and
   final cooling to a hard candy matrix containing chewing gum, said matrix suitable for scoring and cutting, and for grinding into a particulate,
   wherein said base is included in an amount of from about 5% to about 55% by weight, and said cooked candy syrup is included in an amount of from about 45% to about 95% by weight.

2. The chewing gum candy of claim 1 wherein said base is included in an amount of from about 15% to about 40% by weight and said cooked candy syrup is included in an amount of from about 60% to about 83% by weight.

3. The chewing gum candy of claim 1 wherein said hard candy syrup substantially comprises sorbitol syrup cooked to a temperature of from about 171° to about 185° C. before adding said melted chewing gum base.

4. The chewing gum candy of claim 1 wherein said gum base comprises an elastomer selected from the group consisting of natural and synthetic elastomers including polyisobutylene, styrene-butadiene rubber, and isobutyleneisoprene copolymer, resin component, and plasticizers for compatibilizing said elastomer and said resin.

5. The chewing gum candy of claim 1 which is a product having an initial hardness of from about 9.5 lbs. to about 12.8 lbs. as determined by measurement with a penetrometer machine.

6. The chewing gum candy of claim 1 wherein said additive is an artificial sweetener selected from the group consisting of solid natural and synthetic sweeteners including amino acid based sweeteners, dipeptide sweeteners, glycyrrhizin, saccharin and its salts, acesulfame salts, cyclamates, steviosides, talin, dihydrochalcone compounds and mixtures thereof.

7. The chewing gum candy of claim 1 which is ground to a particulate having a size of between about 40 to about 200 mesh.

8. The chewing gum candy of claim 7 wherein said particulate is further ground to a hard candy powder.

9. A method of preparing a sugarless chewing gum candy confection product comprising mixing a melted chewing gum base heated to a temperature of from about 82° C. to about 94° C. with a cooked hard candy syrup of sorbitol at a temperature which renders said gum base and said cooked candy syrup miscible under mild blending conditions to form a substantially single phase continuous plastic chewing gum candy mass,
   mildly blending the resulting mixture under controlled cooling to a temperature of from about 60° C. to 70° C. so that substantially no air is introduced into said mixture, and
   final cooling to a hard candy matrix containing chewing gum, said matrix suitable for scoring and cutting and for grinding into a particulate, wherein said base is included in an amount of from about 5% to about 55% by weight, and said cooked candy syrup is included in an amount of from about 45% to about 95% by weight.

10. A chewing gum hard candy confection, which softens in the mouth to a chewable mass upon mastication which comprises:

a gum base, and a cooked hard candy syrup of sorbitol;

wherein the chewing gum base is mixed with the cooked candy syrup at a temperature which renders the gum base and cooked candy syrup miscible; and the gum base is present in an amount of about 5% to about 55% by weight and the syrup is present in an amount of about 45% to about 95% by weight.

11. The composition of claim 10 further comprising conventional additives selected from the group consisting of coloring agents, emulsifiers, fillers, flavoring agents, flavor enhancers and mixtures thereof.

12. The method of claim 9 further comprising adding conventional additives selected from the group consisting of color agents, emulsifiers, fillers, flavoring agents, flavor enhancers and mixtures thereof under continued mild blending before the final cooling to a hard candy matrix.

* * * * *